United States Patent [19]

Hofstetter, Jr.

[11] 4,148,215
[45] Apr. 10, 1979

[54] APPARATUS FOR MAKING RHEOLOGICAL MEASUREMENTS

[75] Inventor: Edward G. Hofstetter, Jr., Louisville, Ky.

[73] Assignee: General Signal Corporation, Rochester, N.Y.

[21] Appl. No.: 916,459

[22] Filed: Jun. 19, 1978

[51] Int. Cl.² ..................... G01N 11/00; G01N 11/14
[52] U.S. Cl. .......................................... 73/54; 73/59
[58] Field of Search ..................................... 73/54, 59

[56] References Cited

U.S. PATENT DOCUMENTS

| | | | |
|---|---|---|---|
| 2,409,014 | 10/1946 | Bohmer et al. | 73/54 |
| 2,484,761 | 10/1949 | Stock | 73/59 |
| 2,519,378 | 8/1950 | Kilpatrick | 73/59 |
| 3,147,612 | 9/1964 | Evans | 73/59 |
| 3,181,349 | 5/1965 | Jansson | 73/59 |
| 3,285,057 | 11/1966 | DeZurik | 73/59 |
| 3,364,730 | 1/1968 | Wall | 73/59 |
| 3,751,975 | 8/1973 | Katsura | 73/59 |

*Primary Examiner*—Charles Gorenstein
*Attorney, Agent, or Firm*—Martin LuKacher

[57] ABSTRACT

Consistency transmitters are described in which a torsional transducer is used as a flexural mount for a consistency sensor. A torsional force balance loop, in which signals from the transducer operates a torque motor to balance the torsional forces on the transducer corresponding to consistency, provides for instantaneous and continuous measurement of consistency.

15 Claims, 6 Drawing Figures

APPARATUS FOR MAKING RHEOLOGICAL MEASUREMENTS

BACKGROUND OF THE INVENTION

The present invention relates to apparatus for making rheological measurements and particularly to consistency transmitters.

The invention is especially suitable for use in consistency transmitters of the type which utilize a blade sensor as well as in those types of consistency transmitters which utilize a rotating sensor. The invention however is generally applicable for use in apparatus for making various types of rheological measurement in that it affords reliable and cost effective means for implementing such measurements through the use of electronic circuitry.

Blade sensor consistency transmitters determine consistency by sensing the drag imposed by the medium on a sensing blade; the medium being for example, paper stock fiber. The sensor pivots on a flexural mount, and its position is detected by a pneumatic torque transducer. A feedback system including pneumatic actuators tends to maintain the blade sensor position. Such a blade sensor consistency transmitter is available from DeZurik Corporation of Sartell, Minnesota, and is described in their Bulletin 91.001 dated Sep. 1968. The pneumatic force balance system is described in the DeZurik U.S. Pat. No. 3,285,266 and assigned to DeZurik, a unit of General Signal Corp. Another blade sensor consistency transmitter is described in U.S. Pat. No. 3,364,730 issued Jan. 23, 1968. Consistency transmitters may also have rotating sensors which are supported on flexural mounts. As consistency changes, a housing, for a motor which rotates the sensing element, itself rotates on the flexural mounts. The rotational movement of the housing can be detected by a pneumatic torque transducer and a force balance feedback arrangement may be used as described above. Reference may be had to DeZurik U.S. Pat. No. 3,285,057 and Ostroot U.S. Pat. No. 3,285,058 for further information respecting rotating sensor consistency transmitters.

While consistency transmitters utilizing pneumatic torque transducers and force balance feedback system have proven themselves entirely satisfactory in operation, it is desirable that the transducer and feedback system be implemented electronically. The problem of an electronically operating consistency transmitter is not readily solvable by reason of the stringent requirements for reliability and accuracy in the measurements under industrial operating conditions. The movements of the sensor in response to consistency changes are very minute. Electronic systems are inherently sensitive to changes in temperature and changes in pressure which can easily mask any response to consistency changes; thus rendering the measurement inaccurate and unreliable. Furthermore, the consistency measurements are affected by frictional forces which are compensated by reason of the flexural mounts for the sensors. Implementations of electronic sensors affect the mounts and contribute to errors in the consistency measurement.

Various types of electronic transducers, particularly strain gauges have been suggested for detecting flow and other fluid effects (see U.S. Pat. Nos. 2,805,574; 3,098,384; 3,115,777; 3,147,612; 3,238,773; 3,287,971; 3,338,093; 3,796,088; 3,908,458; and Re. 27,354). None of these however provide for electronically sensing consistency changes and balancing of torque in response to such changes so as to provide accurate and reliable measurements of consistency. Moreover, none of the approaches which have been suggested are concerned with the problem of avoiding any adverse effect on the mounting of a consistency sensor.

1. Objects of the Invention

Accordingly, it is a principal object of the present invention to provide improved apparatus for making rheological measurements, and particularly measurements of consistency, through the use of electronic means.

It is a further object of the present invention to provide an improved electronically operative consistency transmitter which is both accurate and reliable in operation.

It is a still further object of the present invention to provide an improved electronically operative consistency transmitter which does not adversely affect the flexural mounting of consistency sensors and yet provides a reliable mount for the rotational movement of the sensor in response to consistency changes.

It is a still further object of the present invention to provide an improved electronically operative consistency transmitter in which measurement errors due to changes in temperature and pressure are minimized.

SUMMARY OF THE INVENTION

Briefly described, a consistency transmitter in accordance with a preferred embodiment of the invention has a sensor which is adapted to be disposed in the flow path of the liquid medium on which consistency measurements are to be made. An electronic transducer provides a flexural mount for the sensor and comprises a flexural member which is supported at its opposite ends to define a torsional axis extending longitudinally of the flexural member. A tube or sleeve is rotatably mounted about the torsional axis and is disposed around the flexural member. The flexural member and sleeve as well as the sensor are attached to each other in torque transmitting relationship. The sleeve serves as a strong and reliable mount without introducing moments or torque, frictional or otherwise, which may alter the rotational movement of the sensor about the torsional axis in response to changes in consistency of the liquid medium. The torsional flexure of the flexural member becomes a function of the pivotal movement of the sensor and therefore of the consistency of the liquid medium. Means such as strain gauge elements are attached to the flexural member and translate the torsional flexure thereof into electrical signals. These signals are used in a force balance system comprising a torque motor which may be coupled to a torque arm of the sensor or otherwise to the sensor eccentrially of the torsional axis of the flexural member. Electronic circuits responsive to the signal from the flexural member, as may be derived from a bridge circuit including the strain gauge elements which are secured to the sensor, operate the motor to apply torque to the flexural member in a sense to counteract and balance the torsional flexure of the flexural member due to changes in consistency. The output torque of the motor or the electrical signal which drives the motor is a measure of consistency and may be applied to a utilization device such as a meter, recorder, or process controller.

The foregoing and other objects, features and advantages of the invention, as well as the preferred embodi-

DESCRIPTION OF THE PREFERRED EMBODIMENT

Figure 1:
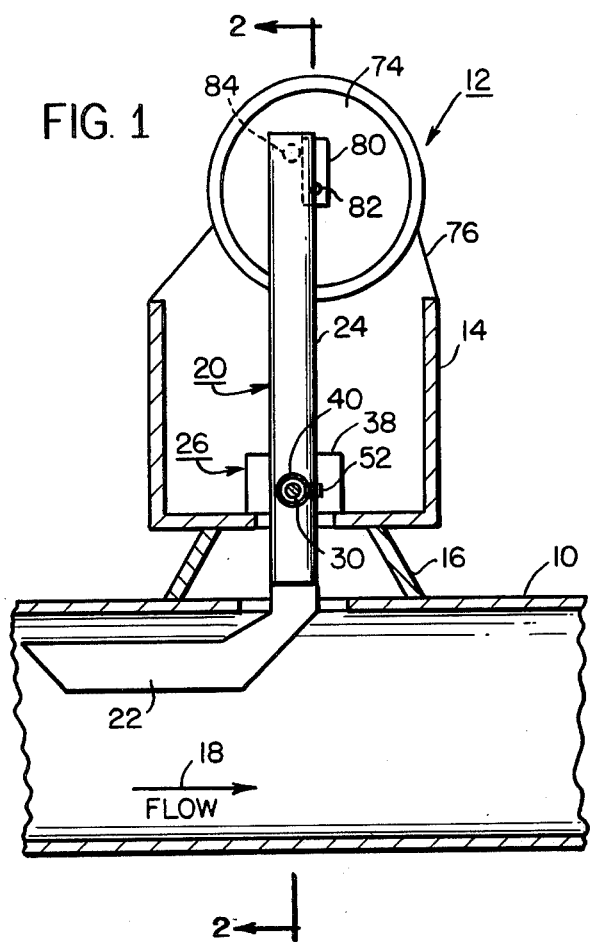
FIG. 1 is a simplified sectional view of a blade sensor consistency transmitter in accordance with the presently preferred embodiment of the invention.
Figure 2:
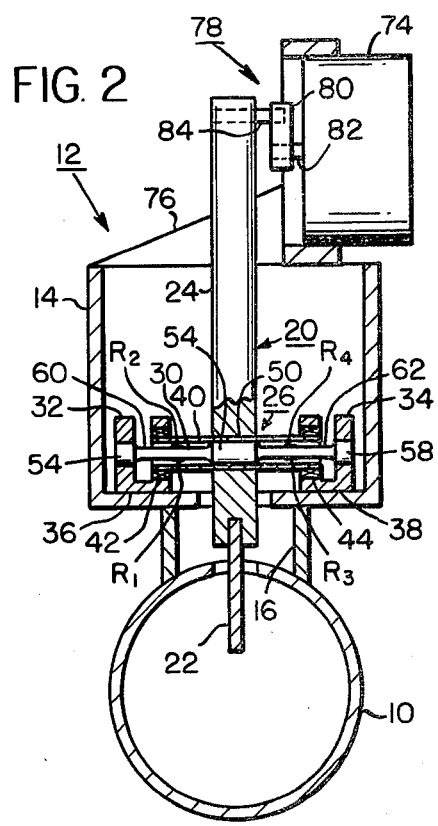
FIG. 2 is a sectional view of the consistency transmitter shown in FIG. 1, the section being taken along the line 2—2 in FIG. 1.
Figure 4:
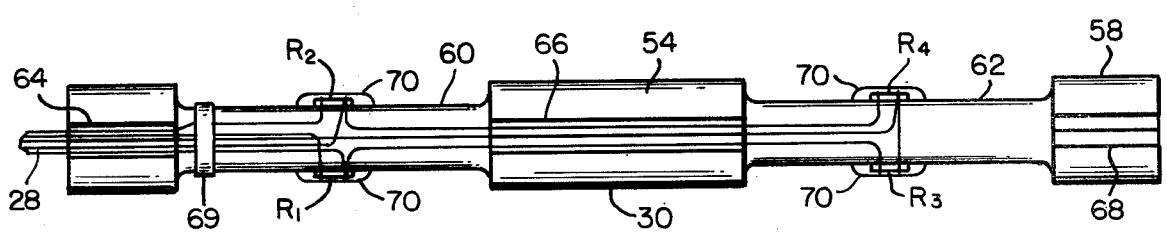
FIG. 4 is an enlarged plan view of the torsional transducer which is part of the flexural mount of the transmitter illustrated in FIGS. 1, 2 and 3.

Referring to FIGS. 1 through 4 of the drawing, there is shown a pipe line 10 on which the consistency transmitter 12 is mounted. The housing 14 of the transmitter 12 is supported on the pipe line 10 by means of a skirt-like flange 16 which may be welded to the pipeline. The consistency of a liquid medium such as stock fiber which flows along the pipe line 10 in the direction indicated by the arrow 18 is measured by the transmitter 12.

A blade sensor 20 in the transmitter 12 consists of a blade sensing element 22 which is secured to a shaft 24. The shaft also provides a torque arm. The sensor 20 is pivotly mounted in a flexural mount 26. The mount or flexure 26 also provides a torsional transducer which translates the pivotal movement of the sensor 20 as in response to consistency changes into electrical signals. Leads 28 which carry these signals (see FIG. 4) are not shown in FIGS. 1, 2 and 3 to simplify the illustration. The torsional axis of the mount is the longitudinal axis of a flexural member 30. A rod, preferably of aluminum, provides the member 30. The rod is clamped at its opposite ends in clamp sections 32 and 34 of mounting blocks 36 and 38.

A support tube or sleeve 40 is disposed around the rod 30. It is arranged centrally of the rod 30. The ends of the sleeve 40 are rotatably mounted in bearings 42 and 44. Bearing sections 46 and 48 of the mounting blocks 36 and 38 retain the bearing 42 and 44. These bearings are preferably ball bearings which minimize frictional forces in the flexural mount 26.

A lateral hole 50 through the shaft 24 receives the flexural mount. The axis of the shaft is perpendicular to the torsional axis of the mount (viz, the axis of the rod 30). The rod 30, the sleeve 40, and the shaft 24 are in torque transmitting relationship. This relationship is established by means of a screw clamp 52 which extends through the shaft 24, the sleeve 40, and into engagement with the rod 30. Torque on the rod is produced by reason of the flow through the pipeline and places the rod into torsional flexure.

In order to make the rod more sensitive to such torsional flexure, the rod is formed with alternate lands and grooves. A central land 54 and end lands 56 and 58 are separated by grooves 60 and 62. The lands 54, 56 and 58 have "V" notches 64, 66 and 68 therein. Since the leads 28 are brought out to the left, only the notches 64 and 66 are used. The other notch 68 may be used if the leads are to be brought out from the opposite end of the rod 30 (ses FIG. 4).

Secured centrally of the grooves 60 and 62 are pairs of strain gauge elements which are indicated as $R_1$ to $R_4$. The elements $R_1$ and $R_2$ are disposed diametrically opposite to each other in the groove 60. The other pair of elements $R_3$ and $R_4$ are also disposed diametrically opposite each other in the groove 62. The element pairs are located centrally of the length of their grooves. Cement may be used to secure the elements to the rods in the grooves 60 and 62. The cement may also be used to secure the leads on the rod. The leads may be brought to a terminal strip 69 and thence from the strip outwardly through the notch 64. Fine magnet wire may be used for the leads which are connected between the terminal strip and the strain gauge elements. Heavier wire may be used from the terminal strip 66 outwardly from the rod 30. The cement, which is shown about the elements as the material 70 which is raised off the surface of the rod may suitably be an epoxy cement. A thin layer of cement is preferred.

Figure 5:
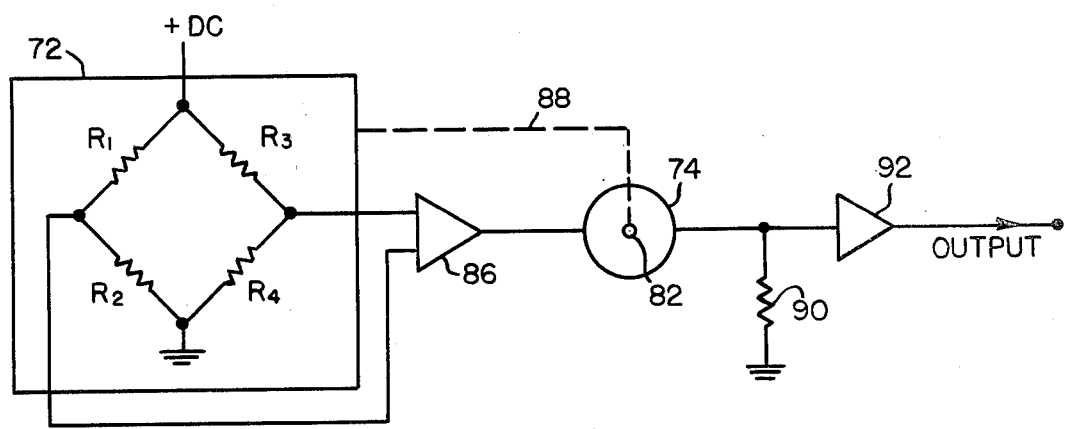
FIG. 5 is a schematic diagram of the electronic circuit of the transmitter shown in FIGS. 1 to 4.

The sleeve 40 encompasses the central land 54 and extends over the grooves 60 and 62 so as to encompass the strain gauge elements. Only torsional flexure is sensed by the strain gauge elements. Changes due to temperature or pressure are linear dimensional changes and do not impose torsional strain on the rod. The linear dimensional changes in the strain gauge elements are automatically compensated in that the elements are disposed in a bridge circuit 72 as shown in FIG. 5. The torsional flexure of the element will increase the strain in those elements, say $R_1$ and $R_3$ which are on the same side, while decreasing the strain on the elements, say $R_2$ and $R_4$ on the opposite side; thus providing an output from the detector arm of the bridge which is maximal for torsional strain. Linear dimensional changes of the rod produces equal strains on all of the elements $R_1$ to $R_4$. Accordingly, such linear changes are compensated for and not reflected in the output from the detector arm of the bridge 72. As shown in FIG. 5 each pair of strain gauge elements forms the opposite side of the bridge (viz., $R_1$ and $R_2$ form one side of the bridge, while $R_3$ and $R_4$ form the other side of the bridge).

A force balancing system for counteracting the torque due to the flow and thereby sensing changes in consistency of the liquid in the pipeline 10 consists of a direct current torque motor 74. This motor is firmly secured to the housing in a casting 76 which is attached to the top of the housing 14. A casting is preferred since it protects the motor against vibration which might affect the measurement. An eccentric coupling 78 between the motor and the torque arm provided by the shaft 24 is used. This coupling consists of an adjustable block 80 on the shaft 82 of the motor and a pin 84 attached to the upper end of the shaft 24. The motor 74 is connected in a feedback loop to the detector arm of the bridge circuit 72 by way of an amplifier 86. This amplifier may be an operational amplifier connected in a differential amplifier mode so as to amplify the output voltage from the bridge when it is unbalanced. The dash line 88 in FIG. 5 represents the coupling from the shaft 82 of the motor 74 through the eccentric coupling 78 and the torque arm at the upper end of the shaft 24 to the torsional flexure rod 30 back to the strain gauge element $R_1$ to $R_4$ of the bridge. The motor is operated to apply torque to cause torsional flexure of the rod about its longitudinal axis. Preferably, the operating point of the amplifier 86 is set so that torque is applied to the rod 30 and it is placed in torsional flexure in the quiescent or static condition of the loop (viz., without flow through the pipeline 10 or with a certain average or steady flow through the pipeline 10. This provides an initial bias on the blade. The system is calibrated to accomodate this bias. As the consistency of the liquid in the pipeline 10 varies, the electrical signal output from the bridge varies correspondingly to the consistency changes. This variation is counteracted by the torque produced by the motor. The torque is a function of the electrical signal from the bridge which is amplified in the amplifier 86. This signal, which is in the form of a current, passes through a resistor 90 in series with the operating winding of the motor 74. The voltage developed across this resistor 90 is amplified in an amplifier 92 and provides an output which represents the consistency of the liquid flowing through the pipeline 10. This output signal is applied to a utilization device such as a recorder or to a process controller, which may for example change the dilution of the pulp stock or other liquid in the pipeline so as to maintain a present consistency thereof.

Figure 6:
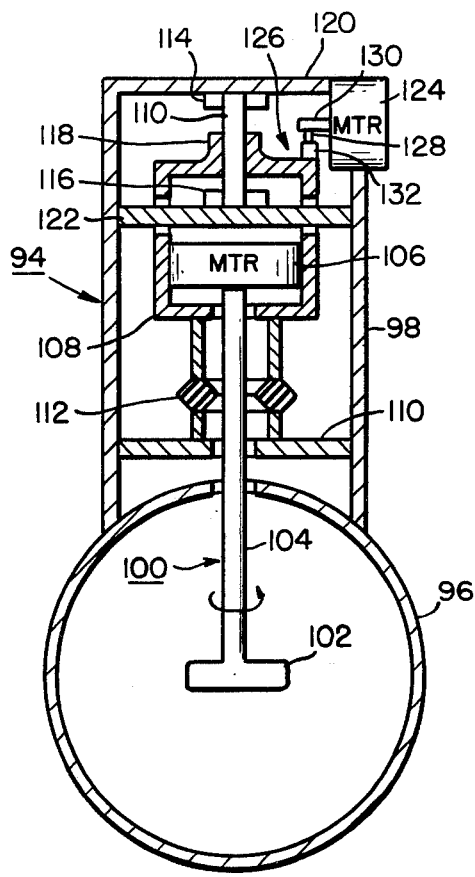
FIG. 6 is a sectional view similar to FIG. 2 and illustrating a rotating sensor consistency transmitter which embodies the invention.
Figure 3:
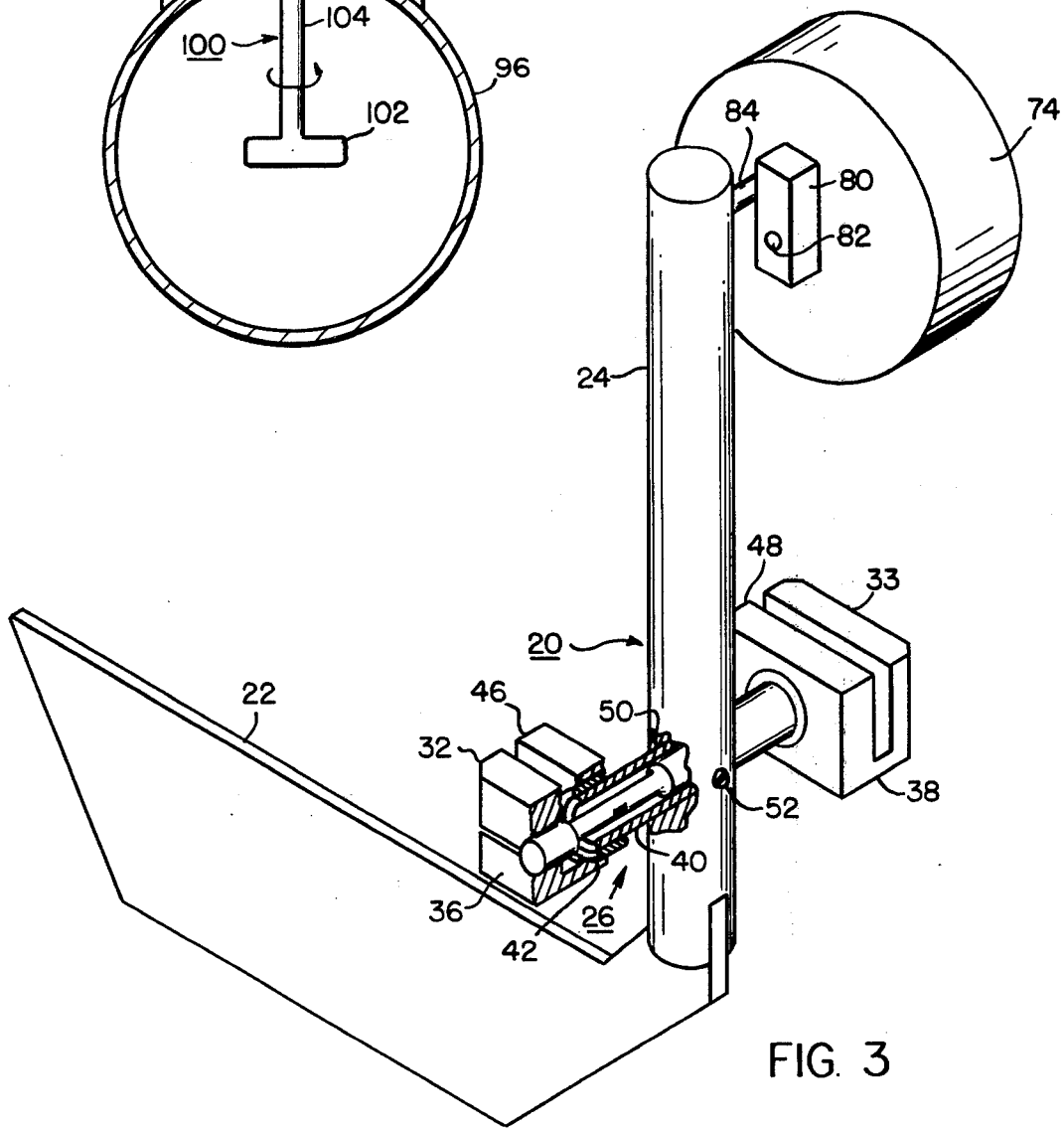
FIG. 3 is an enlarged perspective view showing portions of the consistency transmitter illustrated in FIGS. 1 and 2.

A rotating sensor consistency transmitter 94 is shown in FIG. 6 mounted on a pipeline 96. The transmitter 94 has a housing 98. A rotating sensor 100 is provided by a sensing disc 102 connected to a shaft 104 which is revolved at a constant rate by a motor 106. A motor housing 108 is supported by flexural mounts 110 and 112 in the transmitter housing 98. The flexural mount 110 may be similar to the flexural mount 26. In the mount 110, mounting blocks 114 and 116 support the ends of a flexural rod and a sleeve in a manner similar to the support of the rod 30 and sleeve 40 as was explained in connection with FIGS. 1 through 4. The upper end of the motor housing 108 is formed with a boss 118 which is connected in torque transmitting relationship with the sleeve and flexural rod of the mounting 110 at the center of the sleeve and rod as was explained in connection with FIGS. 1 through 4. The upper mounting block 114 is attached to the roof 120 of the transmitter housing 98. A spider 122 which is a part of the transmitter housing 98 and extends through openings in the motor housing 108 provides support for the lower mounting block 116.

The lower flexural mount 112 is provided by a ring of elastomeric material which may be part of a seal arrangement as explained in the above-referenced DeZurik U.S. Pat. No. 3,285,057. The torsional axis of the amount 110 is colinear with the axis of the shaft 104 and sensing disc 102 of the sensor 100.

As the consistency of the liquid in the pipeline 96 changes, the torque on the flexural rod in the mounting 110 varies correspondingly. This torsional flexure is translated into an electrical signal by means of stain gauge elements located on the rod and arranged in a bridge circuit as was explained in connection with FIGS. 4 and 5. To balance this torque, a dc torque motor 124 similar to the motor 74 is connected by an eccentric coupling 126 to the motor housing 106 at a position radially outward from the longitudinal axis of the rod in the flexural mount 110. The housing thus provides a torque arm. A separate torque arm connected to the flexural mount 110 may alternatively be used. The eccentric coupling consists of a pin 128 connected to the shaft 130 of the motor 124. This pin engages a bar 132 secured to the top of the motor housing 108 and which projects upwardly therefrom.

The flexural mount provides a torsional transducer which produces the electrical signals corresponding to the consistency and consistency changes. These signals control the torque developed by the motor 124 which counter-balances the torsional flexure in the transducer. The current which produces the torque is proportional to the consistency of the liquid in the pipeline 96 and responds accurately to consistency changes. The electrical signal may be recorded or utilized as was explained in connection with FIG. 5.

From the foregoing description, it will be apparent that there has been provided improved apparatus for making rheological measurements and particularly to improve consistency transmitters which have electronic means for developing outputs representing consistency as well as for controlling the consistency transmitter. The blade consistency transmitter is presently the preferred embodiment of the invention. The invention may also be used in rotational consistency transmitters. Modifications and variations in the herein illustrated consistency transmitters within the scope of the invention, will undoubtedly suggest themselves to those skilled in the art. Accordingly, the foregoing description should be taken as illustrative and not in a limiting sense.

What I claim is:

1. In apparatus for making rheological measurements upon a medium having a sensor adapted to be disposed in the flow path of said medium, a transducer arrangement which comprises a flexural member fixedly supported at its opposite ends to define a torsional axis longitudinally of said flexural member, a sleeve rotatably mounted about said torsional axis and disposed around said flexural member, said flexural member and said sleeve being attached to each other in torque transmitting relationship, said sensor also being connected to said sleeve and pivotally mounted about said torsional axis to import torsional flexure to said flexural member as a function of a rheological parameter of said medium, and means attached to said flexural member for translating the torsional flexure thereof into an electrical signal.

2. The invention as set forth in claim 1 further comprising electric motor means connected to said sleeve and responsive to said electrical signal for applying torque to said flexural member in a sense to counteract the torsional flexure of said flexural member due to said rheological parameter, and means for indicating the output torque of said motor as a measure of said parameter.

3. The invention as set forth in claim 2 wherein said sensor comprises a sensing blade, a shaft having said blade at the lower end thereof, said shaft having an axis perpendicular to said torsional axis, a hole in said shaft, said sleeve and flexural member extending through said hole, means securing said shaft, sleeve and flexural member to each other, said shaft extending upwardly from said sleeve and defining a torque arm, and eccentric drive means on said motor engageable with said shaft for driving said shaft.

4. The invention as set forth in claim 2 further comprising means for operating said motor means for applying torque to said flexural member for continuously applying a flexural bias force to said sensor via said flexural member.

5. The invention as set forth in claim 1 further comprising a pair of bearings, a pair of clamps, said bearings being disposed around and rotatably supporting said sleeve and being disposed inwardly of said clamps, said clamps each being in engagement with a different one of the opposite ends of said flexural member.

6. The invention as set forth in claim 1 wherein said flexural member is a cylindrical rod having lands at the center and at each of the opposite ends thereof and grooves between said lands, said translating means comprising first and second pairs of strain gauge elements, said first pair being secured to said rod in one of said grooves and said second pair being secured to said rod in the other of said grooves, said elements in each pair being diametrically opposite each other.

7. The invention as set forth in claim 6 wherein said sleeve encompasses only said grooves and said central land.

8. The invention as set forth in claim 7 wherein said sensor comprises a shaft, a sensing blade attached to one end of said shaft, said shaft having a lateral hole, said central land and the portion of said sleeve which encompasses said central land being disposed in said hole, and means connecting said central land, sleeve and shaft in torque transmitting relationship.

9. In a consistency transmitter having a sensor which is supported in a housing on a flexural mount subject to torque from said sensor as it moves, an improved flexural mount and torque balance system which comprises a torsional transducer which provides said flexural mount, said transducer comprising a rod having a longitudinal axis, said rod being secured to said housing and to said sensor at positions spaced from each other along longitudinal axis such that torque from said sensor causes torsional flexure of said rod about said longitudinal axis, a plurality of strain gauge elements responsive to the torsional flexure of said rod secured to said rod between said positions, means also secured to said rod for applying torque to said rod to cause torsional flexure of said rod about said longitudinal axis, circuit means connected to said strain gauge elements for generating an electrical output representing consistency and corresponding to the torsional flexure of said rod, and a motor attached to said housing and responsive to said electrical output for operating said torque applying means to balance the torque from said sensor.

10. The invention as set forth in claim 9 wherein said rod has a plurality of lands and grooves alternately disposed along said longitudinal axis, said sensor and torque applying means being secured to a first of said lands, and said rod being secured to said housing at a second of said lands, said strain gauge elements being secured to said rod in at least a first of said grooves which is disposed between said first and second lands.

11. The invention as set forth in claim 10 wherein said rod is also secured to said housing at a third of said lands, said third land and said second land being on opposite sides of said first land, said strain gauge elements also being secured to said rod in a second of said grooves which is disposed between said first and third lands.

12. The invention as set forth in claim 11 wherein a first pair of said strain gauge elements are disposed diametrically opposite each other in said first groove and a second pair of said strain gauge elements are disposed diametrically opposite each other in said second groove, said first and second pair of strain gauge elements being connected to each other to define opposite sides of a bridge circuit.

13. The invention as set forth in claim 12 wherein a tube having an inner diameter about equal to the diameter of said lands and a length about equal to the length of said rod across said first groove, said first land and said second groove is disposed around said rod over said first groove, said first land and said second groove, said first land being secured in torque transmitting relationship with said tube, said tube being secured in torque transmitting relationship to said sensor and said torque applying means.

14. The invention as set forth in claim 9 wherein said sensor comprises a second housing in said transmitter housing, said rod being disposed between said transmitter housing and said second housing and supporting said second housing, a second motor in said second housing having a shaft extending from said second housing in a direction opposite from said rod, said shaft having a consistency sensing disc secured at the end thereof, the axes of said shaft and disc and said longitudinal axes being colinear, said means for applying torque to said rod being secured to said housing at a position spaced radially from said longitudinal axis.

15. The invention as set forth in claim 9 wherein said sensor comprises a sensing blade, a shaft secured to said blade, the axis of said shaft being perpendicular to said longitudinal axis of said rod, said rod and shaft being secured to each other whereby said shaft and blade pivot about said longitudinal axis as said rod torsionally flexes, a portion of said shaft extending in a direction away from said blade and defining a torque arm, and means coupling said torque arm and said motor in driving relationship.

* * * * *

UNITED STATES PATENT OFFICE
CERTIFICATE OF CORRECTION

PATENT NO. : 4,148,215
DATED : April 10, 1979
INVENTOR(S) : Edward G. Hofstetter, Jr.

It is certified that error appears in the above-identified patent and that said Letters Patent are hereby corrected as shown below:

In the claims:

Column 6, line 39    "import" should read --impart--.

Column 7, line 32    "longitudinal axis" should read --said longitudinal axis--.

Signed and Sealed this

Eleventh Day of December 1979

[SEAL]

Attest:

SIDNEY A. DIAMOND

Attesting Officer    Commissioner of Patents and Trademarks